US008008446B2

(12) United States Patent
Hofbauer et al.

(10) Patent No.: US 8,008,446 B2
(45) Date of Patent: Aug. 30, 2011

(54) AUTO-ANTIBODIES AGAINST THE MELANOCORTIN-4 RECEPTOR

(75) Inventors: Karl Hofbauer, Basel (CH); Jean-Christophe Peter, Ammerschwihr (FR)

(73) Assignee: University of Basel (CH)

( * ) Notice: Subject to any disclaimer, the term of this patent is extended or adjusted under 35 U.S.C. 154(b) by 0 days.

(21) Appl. No.: 12/347,153

(22) Filed: Dec. 31, 2008

(65) Prior Publication Data

US 2009/0191219 A1 Jul. 30, 2009

Related U.S. Application Data

(60) Provisional application No. 61/018,370, filed on Dec. 31, 2007.

(51) Int. Cl.
*C07K 16/00* (2006.01)
*C12P 21/08* (2006.01)

(52) U.S. Cl. .............. 530/387.9; 530/388.22; 530/389.1

(58) Field of Classification Search ........................ None
See application file for complete search history.

(56) References Cited

U.S. PATENT DOCUMENTS

| | | | |
|---|---|---|---|
| 4,690,905 A | 9/1987 | Diamond | |
| 4,734,433 A | 3/1988 | Drabek | |
| 5,703,220 A | 12/1997 | Yamada et al. | |
| 5,908,609 A * | 6/1999 | Lee et al. | 424/9.2 |
| 6,117,975 A | 9/2000 | Yamada et al. | |
| 6,287,763 B1 | 9/2001 | Lee et al. | |
| 6,537,760 B1 | 3/2003 | Bergmann et al. | |
| 6,573,070 B1 * | 6/2003 | MacNeil et al. | 435/69.1 |
| 7,034,004 B2 | 4/2006 | Haskell-Luevan et al. | |
| 7,169,777 B2 | 1/2007 | Backer et al. | |
| 2004/0082779 A1 | 4/2004 | Vos et al. | |
| 2007/0123453 A1 | 5/2007 | Heiman et al. | |

FOREIGN PATENT DOCUMENTS

| | | |
|---|---|---|
| EP | 0915706 A1 | 12/1997 |
| EP | 1167386 A1 | 2/2002 |
| WO | 9747316 | 12/1997 |
| WO | 9810068 A2 | 3/1998 |
| WO | 9826294 | 6/1998 |
| WO | 0185930 A2 | 11/2001 |
| WO | 03014742 A2 | 2/2003 |

OTHER PUBLICATIONS

Program for the Assessment of Clinical Cancer Tests, http://cancerdiagnosis.nci.nih.gov/assessment/progress/markerdev.htm, downloaded Feb. 3, 2010.*
Hawkins 2004. Obesity Res. 12:107S-114S.*
Gantz et al., "Molecular Cloning, Expression, and Gene Localization of a Fourth Melanocortin Receptor," Journal of Biological Chemistry, 268(20), Jul. 15, 1993, pp. 15174-15179.
Cowley, "Hypothalamic Melanocortin Neurons Integrate Signals of Energy State," European Journal of Pharmacology, 480, 2003, pp. 3-11.
Elies et al., "Immunochemical and Functional Characterization of an Agonist-Like Monoclonal Antibody Against the M2 Acetylcholine Receptor," European Journal of Biochemistry, 251, 1998, pp. 659-666.
Peter et al., "Antibodies Against the Melanocortin-4 Receptor Act as Inverse Agonists In Vitro and In Vivo," American Journal of Physiology: Regulatory, Integrative and Comparative Physiology, 292(6), 2007, pp. R2151-R2158.
Oi et al., "Lymphocyte Membrane IgG and Secreted IgG Are Structurally and Allotypically Distinct," Journal of Experimental Medicine, 151, May 1980, pp. 1260-1274.
Mountjoy et al., "Localization of the Melanocortin-4 Receptor (MC4-R) in Neuroendocrine and Autonomic Control Circuits in the Brain," Molecular Endocrinology, 8, 1994, pp. 1298-1308.
Peter et al., "Anti-Melanocortin-4 Receptor Autoantibodies in Obesity," Journal of Clinical Endocrinology & Metabolism, 94 (3), 2009, pp. 793-800.
Biozentrum University of Basel Biennial Report 2006-2007, University of Basel, 2007 available at http://www.biozentrum.unibas.ch/report0607/biennial_0607_print.pdf.
Peter et al., "Pharmacologically Active Monoclonal Antibody Against the Human Melanocortin-4 Receptor as a Possible Treatment of Cachexia," MipTec—The Leading European Event for Drug Discovery, Poster Session 1, Oct. 15, 2008, available at http://registration.akm.ch/einsicht_miptec.php? XNABSTRACT_ID=76605 &XNSPRACHE_ID=2&XNKONGRESS_ID=80 &XNMASKEN_ID=900.
Hofbauer et al., "Antibodies as Pharmacologic Tools for Studies on the Regulation of Energy Balance," Nutrition, 24 (9), 2008, pp. 791-797.

* cited by examiner

*Primary Examiner* — Shulamith H Shafer
(74) *Attorney, Agent, or Firm* — Joyce von Natzmer; Pequignot + Myers LLC

(57) ABSTRACT

Disclosed are biological markers for obesity and methods for diagnosing and treating obesity and related conditions by detecting and modulating the activity of auto-antibodies against the melanocortin-4 receptor or a portion of the melanocortin-4 receptor. Also disclosed are methods for discovering new therapeutics which modulate the activity of auto-antibodies against the melanocortin-4 receptor or a portion of the melanocortin-4 receptor, in particular which prevent the binding of auto-antibodies against the melanocortin-4 receptor or a portion of the melanocortin-4 receptor.

7 Claims, 5 Drawing Sheets

1    MNSTHHHGMYTSLHLWNRSSHGLHGNASESLGKGHSDGGCYEQLFVSPEVFVTLGVISLL

61   ENILVIVAIAKNKNLHSPMYFFICSLAVADMLVSVSNGSETIVITLLNSTDTDAQSFTVN

121  IDNVIDSVICSSLLASICSLLSIAVDRYFTIFYALQYHNIMTVRRVGIIISCIWAACTVS

181  GVLFIIYSDSSAVIICLITMFFTMLVLMASLYVHMFLMARLHIKRIAVLPGTGTIRQGAN

241  MKGAITLTILIGVFVVCWAPFFLHLLFYISCPQNPYCVCFMSHFNLYLILIMCNAVIDPL

301  IYALRSQELRKTFKEIICFYPLGGICELPGRY (SEQ ID NO:1)

FIG. 1

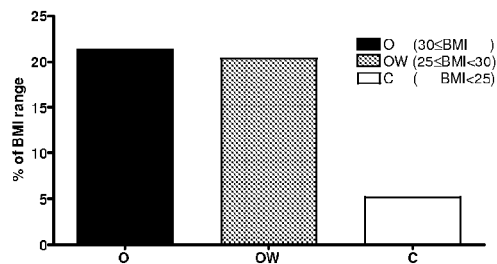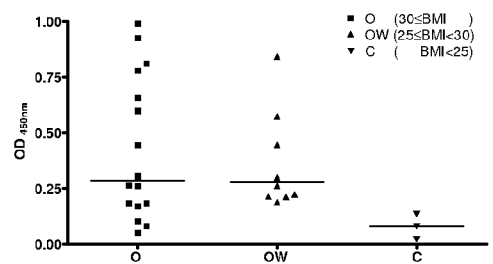
FIG. 4A
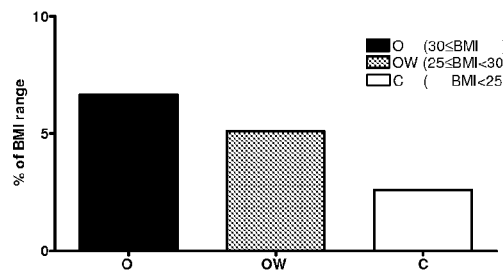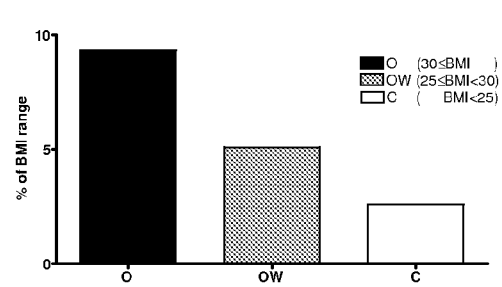
FIG. 4B
FIG. 4C
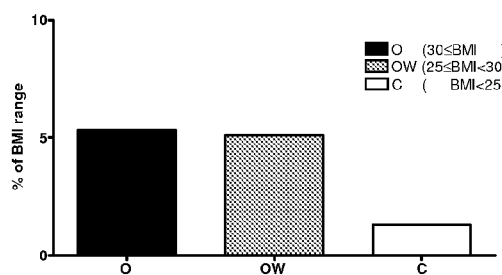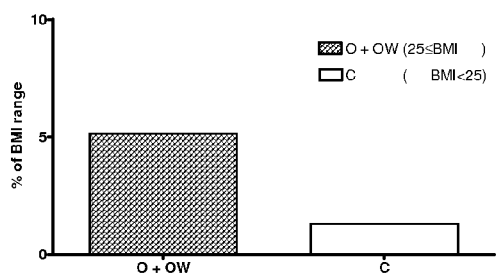
FIG. 4D

AUTO-ANTIBODIES AGAINST THE MELANOCORTIN-4 RECEPTOR

RELATED APPLICATION DATA

This application claims priority to and the benefit of the filing date of U.S. Provisional Patent Application No. 61/018,370, entitled METHODS FOR DIAGNOSING AND TREATING OBESITY BY MODULATING THE ACTIVITY OF AUTO-ANTIBODIES AGAINST THE MELANOCORTIN-4 RECEPTOR, filed on Dec. 31, 2007, the entirety of which is hereby incorporated by reference.

FIELD OF THE INVENTION

The present invention relates to biological markers for obesity and methods for diagnosing and treating obesity and related conditions by detecting and modulating the activity of auto-antibodies against the melanocortin-4 receptor or a portion of the melanocortin-4 receptor. The present invention further relates to methods for discovering new therapeutics which modulate the activity of auto-antibodies against the melanocortin-4 receptor or a portion of the melanocortin-4 receptor, in particular which prevent the binding of auto-antibodies against the melanocortin-4 receptor or a portion of the melanocortin-4 receptor.

BACKGROUND OF RELATED TECHNOLOGY

Obesity is a condition in which the natural energy reserve, stored in the fatty tissue of humans and other mammals, is increased to a point where it is associated with certain health conditions or increased mortality. Although obesity is an individual clinical condition, it is increasingly viewed as a serious and growing public health problem, as excessive body weight has been shown as a predisposition to various diseases including cardiovascular diseases, diabetes mellitus type 2, sleep apnea and osteoarthritis. Worldwide, it is estimated that more than 250 million people are obese, and it is a condition that is increasing at an alarming rate. In the US, it is estimated that up to 32% of children may be obese, and experts estimate that up to 50% of the adult population in the US may be obese within a generation.

Conventional treatment for obesity includes dietary modification, and pharmacotherapy for which only three drugs are typically prescribed: phentermine which is a short-term therapy, and orlistat (XENICAL) and sibutramine (MERIDIA/REDUCTIL) which are suitable for long-term treatment. However, pharmacotherapy with these drugs is generally only recommended in obese patients with a BMI>30 $kg/m^2$ or in patients with a lower BMI who have android obesity (an obesity type more commonly associated with serious morbidity and mortality). As such, there is a continuing need to develop new therapeutics for use in the treatment of obesity and related conditions.

In this regard, the hypothalamic melanocortin-4 receptor (MC4-R) is part of a central appetite reducing (anorexigenic) pathway, and it is known that mutations of this receptor can lead to a loss of function and result in severe obesity. MC4-R is a G-protein coupled receptor (GPCR) which has been shown to be expressed primarily in the brain (Gantz et al., 1993, *J. Biol. Chem.* 268:15174-15179; Mountjoy et al., 1994, Mol. Endo. 8:1298-1308) and is known to play a crucial role in energy balance (Cowley, M A, *Eur. J. Pharmacol.* 480:3-11, 2003; Elies, R. et al. *Eur. J. Biochem.* 251:659-666, 1998). The sequences of the MC4-R have been reported in the literature. In this regard, see for example European Patent Application No. 1167386 (canine and feline sequences) and U.S. Pat. Nos. 5,703,220 and 6,117,975 (human sequences). The rat sequence is known to consist of 332 amino acid residues (NCBI Accession No. NP037231).

The MC4-R has been a target of research interest in the treatment of body weight disorders (see, for example, PCT Patent Application Publication No. 97/47316 which discloses drug screening assays for identifying therapeutics useful for such purposes), and non-antibody compounds and polyclonal antibodies that affect the activity of the MC4-R have been reported (see in this regard, for example, U.S. Pat. No. 7,169,777, US Patent Publication No. 2004/0082779, European Patent Application No. 1167386, PCT Publication Nos. WO 01/085930 and 98/10068, and Peter et al., *Am. J. Physiol. Regul. Integr. Comp. Physiol.* 292:R2151-R2158, 2007). Further, although various methods for detecting/identifying auto-antibodies are known for various diseases and conditions, none are known for obesity (see, in this regard for example, European Patent Nos. 0943098 and EP 145662, PCT Patent Publication No. WO 03/014742, and U.S. Pat. No. 4,690,905).

Accordingly, there exists needs to develop new and improved diagnostic and therapeutic methods and agents for obesity and related conditions, and in particular that involve the MC4-R. It is to these needs that the present invention is directed.

SUMMARY OF THE INVENTION

It is an object of the present invention to provide methods for diagnosing and treating obesity and related conditions by detecting and modulating the activity of auto-antibodies against the melanocortin-4 receptor or a portion of the melanocortin-4 receptor. It is further an object of the present invention to provide methods for discovering new therapeutics which modulate the activity of auto-antibodies against the melanocortin-4 receptor or a portion of the melanocortin-4 receptor, in particular which prevent the binding of auto-antibodies against the melanocortin-4 receptor or a portion of the melanocortin-4 receptor.

In this regard, in one embodiment of the present invention there is provided a biological marker for obesity, comprising an isolated auto-antibody or fragment thereof that binds to the melanocortin-4-receptor or a portion of the melanocortin-4-receptor.

In some embodiments of the present invention, the auto-antibody or fragment thereof binds to a portion of the melanocortin-4 receptor comprising the amino acid sequence set forth in SEQ ID NO:2.

In some embodiments of the present invention, the auto-antibody or fragment thereof is detected in a patient's sera by subjecting the sera to an enzyme-linked immunosorbent assay.

In some embodiments of the present invention, the enzyme-linked immunosorbent assay is conducted using a peptide comprising the amino acid sequence set forth in SEQ ID NO:2.

In some embodiments of the present invention, there is provided a method for decreasing the appetite of a mammal, comprising modulating the activity of an auto-antibody present in the patient that binds to the melanocortin-4-receptor or a portion of the melanocortin-4-receptor.

In some embodiments of the present invention, the activity of an auto-antibody is modulated by administering to the patient a compound that prevents the auto-antibody from binding to the melanocortin-4-receptor or a portion of the melanocortin-4-receptor.

In some embodiments of the present invention, the auto-antibody is prevented from binding to a portion of the melanocortin-4-receptor comprising the amino acid sequence set forth in SEQ ID NO:2.

In some embodiments of the present invention, there is provided a method for screening compounds to determine their therapeutic utility in the treatment of overeating disorders, comprising testing the ability of compounds to prevent an auto-antibody from binding to the melanocortin-4-receptor or a portion of the melanocortin-4-receptor.

In some embodiments of the present invention, the ability of the compounds is tested to prevent an auto-antibody from binding to a portion of the melanocortin-4-receptor comprising the amino acid sequence set forth in SEQ ID NO:2.

In some embodiments of the present invention, there is provided a method for diagnosing obesity in a mammal, comprising screening the sera of the mammal for auto-antibodies that binds to the melanocortin-4-receptor or a portion of the melanocortin-4-receptor.

In some embodiments of the present invention, the prevalence of the auto-antibodies in the sera of the mammal is compared to the prevalence of the auto-antibodies in control sera.

BRIEF DESCRIPTION OF THE DRAWINGS

FIG. 1 shows the amino acid sequence of the rat melanocortin-4 receptor.

FIGS. 4A-4D show the distributions of patient populations defined as positive for auto-antibodies against the MC4-R following various experiments.

DETAILED DESCRIPTION OF CERTAIN EMBODIMENTS

Figure 2:
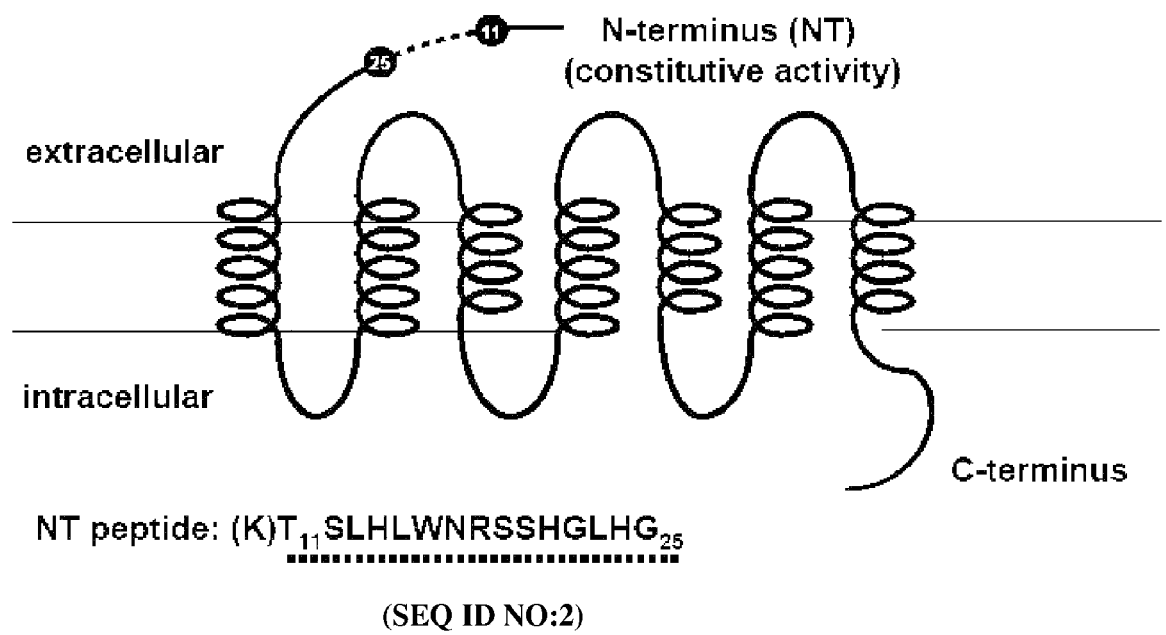
FIG. 2 illustrates the location and amino acid sequence of the N-terminal domain of the MC4-R.

For a more complete understanding of the present invention, reference is now made to the following description of various illustrative and non-limiting embodiments thereof, taken in conjunction with the accompanying figures which are presented to further describe the invention and assist in its understanding. In the figures of the present invention, the nucleotide and amino acid sequences are represented in their conventional orientations and by their standard one-letter abbreviations.

The present invention is directed to methods for diagnosing and treating obesity and related conditions by modulating the activity of auto-antibodies against the melanocortin-4 receptor. As described herein, it has been found in the present invention that auto-antibodies to the MC4-R are about two-fold more prevalent in overweight and obese individuals than in normal or underweight individuals. In the present invention, the functional properties of these auto-antibodies to the MC4-R have been characterized and it has been found that they block the activity of the MC4-R. Animal immunization studies have shown that such auto-antibodies cause a mild form of obesity in rats. Accordingly, detection of these auto-antibodies in mammals serves as a marker for obesity and in general for the propensity for the mammal to become overweight, and modulation of the activity of these auto-antibodies, in particular preventing their binding with the MC4-R provides therapeutic treatment for overweight conditions and obesity.

Unless expressly stated otherwise, all terms used herein are given their conventional art-recognized definitions which will be readily apparent to those of skill in the art. For example and without limitation, "auto-antibodies" include antibodies that are manufactured by a patient's immune system that are directed against one or more of the patient's own proteins.

The following non-limiting Examples set forth the materials and methods utilized in the present invention.

EXAMPLE

Testing of Sera from Various Populations

1. Human Sera 129 sera were obtained from Baden-Baden Stadtklinik, Medizinische Klinik I, Germany. The patients suffered from metabolic diseases and had different body mass indices (BMI): obese individuals (BMI≧30; n=34), overweight individuals (25≦BMI<30; n=43), and control (normal weight or underweight) individuals (BMI<25; n=52).

84 sera were obtained from Strasbourg University Hospital, France. These patients also suffered from metabolic diseases and had different BMI: obese individuals (n=46), overweight individuals (n=17) and control (normal or underweight) individuals (n=24). Data about the 2 populations are summarized in Table I, as follows: (A) German Population; (B) French Population; (C) Mixed Population (Data are presented as mean +/−SD). Sera from Swedish healthy individuals with a normal BMI were used as standards for the settings of the direct ELISA procedure as described in Kamel, R. et al., J. Autoimmun. 2005; 25(1):72-6.

TABLE I

|  | Obese | Over Weighted | Control |
|---|---|---|---|
| (A): German Population | | | |
| Age (years) | 66.3 +/- 15.4 | 72.1 +/- 14.2 | 65.9 +/- 18.4 |
| Female/Male | 22/12 | 19/24 | 34/18 |
| Mean BMI (kb/m$^2$) | 34.6 +/- 4.1 | 26.8 +/- 1.2 | 21.9 +/- 2.3 |
| (B): French Population | | | |
| Age (years) | 59.9 +/- 12.1 | 56.5 +/- 9.8 | 46.6 +/- 14.7 |
| Female/Male | 27/19 | 8/9 | 12/12 |
| Mean BMI (kb/m$^2$) | 37.0 +/- 4.1 | 27.2 +/- 1.7 | 22.2 +/- 1.1 |
| (C): Mixed Population | | | |
| Age (years) | 62.6 +/- 13.9 | 67.4 +/- 14.7 | 59.8 +/- 16.7 |
| Female/Male | 49/31 | 27/33 | 46/30 |
| Mean BMI (kb/m$^2$) | 35.9 | 26.9 +/- 1.4 | 22.0 +/- 1.7 |

Figure 3:
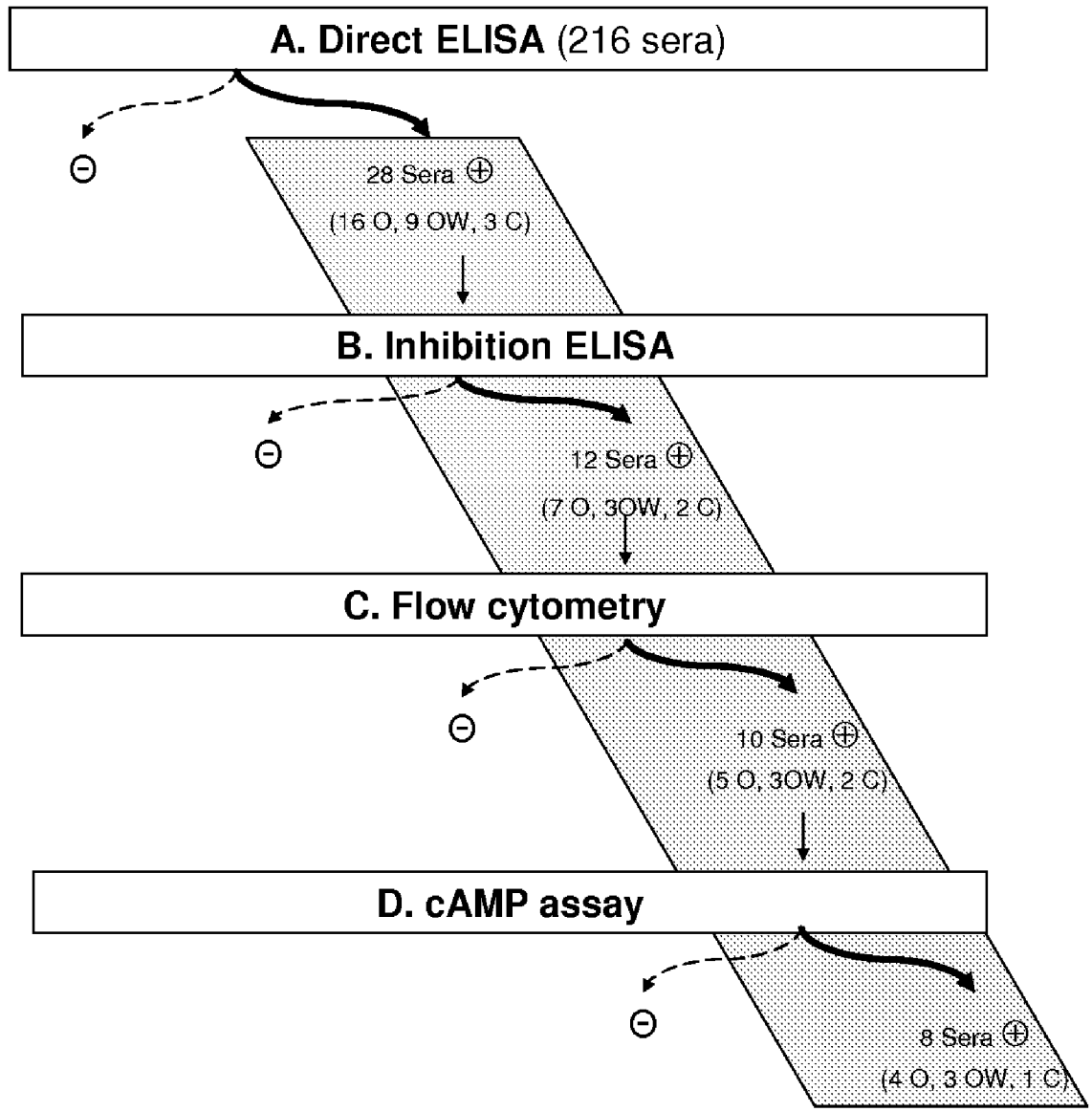
FIG. 3 shows an overview of the experimentation conducted in the present invention.

Turning to FIG. 3, the general approach taken in the present invention is shown in flowchart form, with the number of positive sera at each step of the process shown. As discussed in greater details below, ELISA screening was performed on the NT4 peptide (Step "A"), designed to detect the presence of anti-NT4 IgG in sera of individuals. Next, inhibition ELISA was performed (Step "B") to confirm the specificity of the signal obtained Step A, followed by flow cytometry experiments which were designed to determine if the anti-NT4 antibodies were also able to recognize the native hMC4R at the surface of HEK-293 cells (Step "C"). Finally a cAMP assay was run as the final round of the screening, designed to detect a possible pharmacological activity of the anti-hMC4R Abs.

Only sera positive for all the steps were considered for the final evaluation, as shown in FIG. 4D (left and right panels). Results are presented as numbers of positive sera from obese individuals (O), overweight individuals (OW) and control individuals (C).

2. NT4 Peptide Synthesis

The amino acid sequence of the rat MC4-R consists of 332 amino acid residues (SEQ ID NO:1; NCBI Accession No. NP037231) as shown in FIG. 1. In the present invention, a peptide corresponding to the N-terminal domain of the MC4-R ("NT4 peptide", illustrated in FIG. 2) was synthesized as described in Neimark J and Briand J P.,*Pept. Res.* 1993; 6(4):219-28. The NT4 peptide has the amino acid sequence TSLHLWNRSSHGLHG (SEQ ID NO:2) consisting of residues 11-25 of the rat MCR4-R (see Peter J C et al.,*Am. J. Physiol. Regul. Integr. Comp. Physiol.* 2007; 292 (6):R2151-8).

3. Direct ELISA

The direct ELISA procedure was described in Kamel, R. et al., *J. Autoimmun.* 2005; 25(1):72-6. Briefly, NT4 peptide was adsorbed (20 nM) in carbonate buffer ($Na_2CO_3$ 15 mM; $NaHCO_3$ 35 mM; pH 12.0) on a 96-wells plate (Nunc, Roskilde, Denmark) for 2 hours at 37° C. Plates were blocked with Phosphate Buffered Saline (PBS) (NaCl 150 mM, KCl 2.7 mM, $Na_2HPO_4$ 8 mM, $KH_2PO_4$ 1.8 mM) supplemented with 0.5% Bovine Serum Albumin (Roche, Mannheim, Germany) and 0.05% Tween 20 (Sigma Aldrich, St Louis, USA) (PBST-BSA) for 1 hour at room temperature (RT). Sera were incubated at a dilution of 1/100 in PBS-T-BSA for 1 hour at RT. Plates were washed with PBS supplemented with 0.05% Tween 20 (PBST) and incubated with goat anti-human IgG peroxidase-conjugated (Jackson ImmunoResearch Laboratories, Baltimore, Pike), diluted 1/5000 in PBST-BSA for 1 hour at RT.

Thereafter, plates were washed with PBS-T and PBS. Bound antibodies were revealed with the peroxidase substrate $H_2O_2/3,3',5,5'$-tetramethylbenzide. Reactions were stopped after 7 minutes by adding HCl 1N. The absorbance was measured with Multiskan EX from Biosystems microplate reader at 450 nm. The positivity threshold optical density (OD) value was determined as the mean OD value obtained with 16 standard sera+1.96 SD.

FIG. 4A (left panel) shows the distribution of the population of individuals for which sera were defined as direct ELISA positive. As shown, the number of obese and overweight individuals is about 4 times higher compared to control individuals in the direct ELISA positive population.

FIG. 4A (right panel) shows the optical density obtained in the direct ELISA procedure of each positive sera. As shown, the intensity of the $OD_{450nm}$ is stronger in the obese and overweight population as compared to the control one. Horizontal bars represent the geometric mean of the $OD_{450nm}$ for each BMI class.

4. Inhibition Immunoassay

In order to confirm the specificity of the signal observed for positive sera in direct ELISA, an inhibition immunoassay was set-up to titrate the positive sera preincubated with increasing amounts ($2.10^{-18}$ to $2.10^{-6}$ M) of the NT4 peptide in solution. Specificity was defined as an inhibition≧20%.

FIG. 4C shows the distribution of the population of individuals for which sera were defined as inhibition ELISA positive. As shown, the number of obese and overweight individuals is respectively 4 and 2 times higher compared to control individuals in the inhibition ELISA positive population. Results are presented as percentage of the BMI range.

5. Immunoglobulin Fraction Precipitation

Ig fractions were prepared from 500 μL of serum samples by ammonium sulphate precipitation at a final saturation of 33%. Precipitated sera were placed on ice for 1 hour, and centrifuged at 10400 g during 20 minutes. The pellets were re-suspended with 300 μL of PBS and were extensively dialyzed at +4° C. against PBS for 96 hours.

6. Human Embryonic Kidney 293 (HEK-293) Cell Culture

HEK-293 cells overexpressing the human MC4R (HEK-hMC4R) were cultured in Dulbecco's Modified Eagle's Medium (DMEM; Sigma, St Louis, Mo.) completed with 10% foetal calf serum (Bioconcept, Allschwil, Switzerland) and 1% penicillin/streptomycin (GIBCO, Grand Island, N.Y.) and 600 $μg.mL^{-1}$ G418 antibiotic (Sigma) in a humidified atmosphere containing 5% $CO_2$ at 37° C.

7. Flow Cytometry Assay

In order to check whether the antibodies present in the IgG fraction were able to recognize the hMC4R, flow cytometry assays were performed. Seventy eight IgG fractions from direct ELISA positive sera (n=28) and direct ELISA negative sera (n=50) were submitted to the following procedure. HEK-293-hMC4R cells were fixed with paraformaldehyde at 2% for 2 minutes and then washed with FACSFlow™ (FACS buffer; BD Bioscience, San José, Calif., USA) and incubated 1 hour at 37° C. with IgG fractions diluted 50 fold in FACS buffer. The cells were then washed and incubated with a rabbit anti-human IgG antibody (Jackson ImmunoResearch Laboratories, Baltimore, USA) at a dilution 1/1000 for 30 minutes at 37° C.

The labelling used was a fluorescein isothiocyanate (FITC)-conjugated goat anti-rabbit IgG antibody (BD Biosciences) dilution 1/1000 in FACS buffer; cells were incubated with FITC-conjugates for 30 minutes at 37° C. The fluorescence was detected by FACSCalibur from Beckton Dickinson and Cell Quest was used to acquire data. Data analysis was done with WinMDI 2.9 software. IgG fractions which lead to an increase of fluorescence are considered as positive.

FIG. 4D shows the distribution of the population for which sera were able to recognize the hMC4R at the surface of cells (FACS positive). The number of obese and overweight individuals is higher in the FACS positive population.

8. Cyclic AMP Assay

In order to assess ability of auto-Abs to modulate the receptor activity, cAMP assay was performed on HEK-hMC4R cells. HEK-MC4R cells were transferred to 24-well culture plates and grown until 80% of confluence. Then, cells were washed for 4 h with DMEM (Sigma), after washing the medium was replaced by DMEM containing 100 μM IBMX (Sigma). Cells were pre-incubated with IgG fraction dilution 1/100 or PBS supplemented with 0.1% BSA and IBMX 100 μM for 30 minutes and then treated with increasing concentrations of α-MSH ($10^{-10}$ to $10^{-5}$ M) or were treated 30 minutes with serial dilution of IgG fractions (1/100 to 1/312500 in PBS supplemented with 1 μM of forskolin). The cells were lysed with Biotrak cAMP lysis buffer, and cAMP content was measured using Biotrak cAMP Enzyme immunoassay system kit (Amersham Biosciences, Uppsala, Sweden) as described in the manufacturer's instructions. Protein concentration of the cells lysate was determined using BCA kit (Pierce, Rockford, Ill., USA).

The ratio between the concentration of cAMP and protein was calculated in order to normalize results in function of cells number/wells. This ratio was expressed in percentage of basal cAMP content (for the Abs treatment) or in percentage of maximum cAMP content (for α-MSH±Abs treatment). All data are expressed as mean±SEM. Data were analyzed by Student t-test using Graph Pad Prism 4 Software. IgG fractions were considered as cAMP positive when the MC4R activity was decreased, i.e. by a decrease of cAMP production in basal condition or in presence of α-MSH or by an increase of the EC50 (shift to the right of the concentration-response curve) of α-MSH.

FIG. 4D (left panel) shows distribution of the population of individuals for which sera were able to block the hMC4R (cAMP positive). The number of obese and overweight individuals is 5 times higher as compared to control individuals in the cAMP positive population. FIG. 4D (right panel) shows that when the obese and overweight individuals cAMP positive are combined, their number is 5 times higher than that of the control individuals. Results are presented as percentage of the BMI range.

Figure 5A:
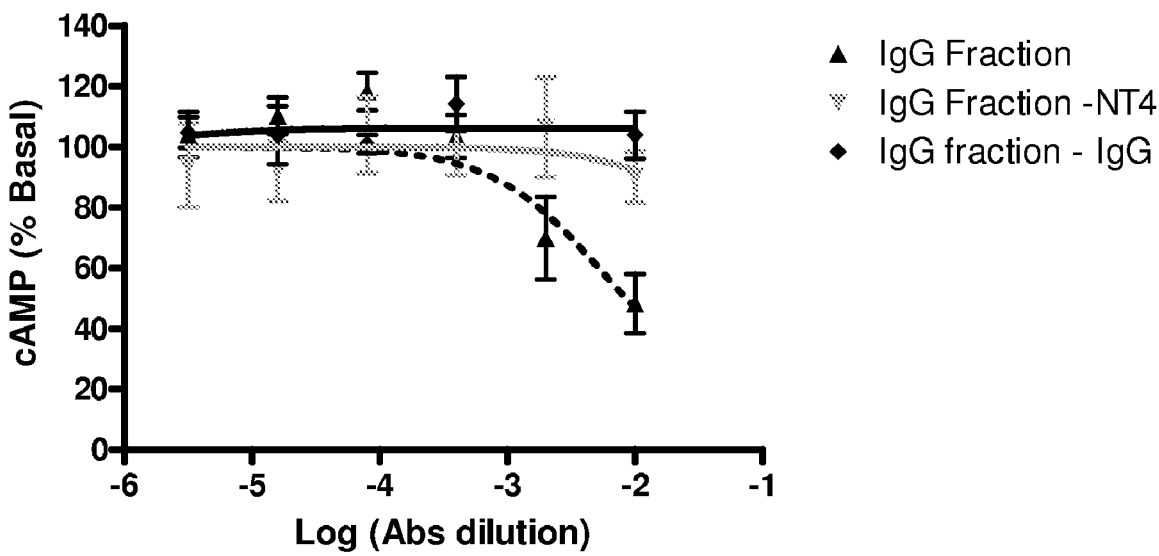
FIGS. 5A and 5B show the functional activity of the auto-antibodies against HEK-293 cells expressing the MC4-R.

As shown in FIG. 5A, cAMP was measured upon treatment of these cells with increasing concentration of IgG fraction. This IgG fraction was able to decrease in a dose dependent manner the basal cAMP content of the cell suggesting an inverse agonist activity of the IgG fraction on the hMC4R(▲). A depletion of IgG (◆) with protein A/G or of anti-NT4 IgG (✹) decreased the inverse agonist activity of this IgG fraction suggesting that the inverse agonist effect of these IgG fraction is due to the presence of anti-NT4 IgG.

Figure 5B:
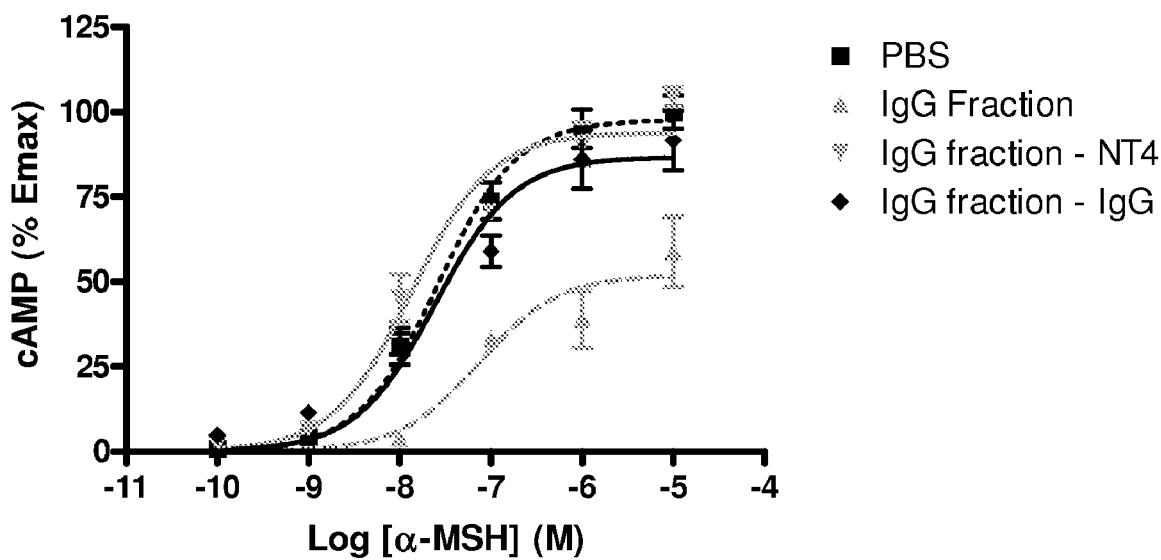

As shown in FIG. 5B, cAMP was measured upon a treatment with increasing concentrations of the MC4R agonist α-MSH in presence (▲) or in absence (■) of a 1/100 dilution of the IgG fraction. The presence of the IgG fraction decreased the maximum efficacy of α-MSH suggesting a non-competitive antagonist properties of this IgG fraction. A depletion of IgG (◆) with protein A/G or of anti-NT4 IgG (✹) did not affect the efficacy of α-MSH suggesting that the blockade of the MC4R is due to the presence of an anti-NT4 IgG.

9. Anti-NT4 AutoAbs Purification

The anti-NT4 autoAbs were affinity-purified on NT4 peptide coupled by their N-terminus to an activated CNBr-Sepharose 4B column (Amersham Biosciences, Uppsala, Sweden) according to manufacturer's instructions. Culture supernatants were loaded on the column at 4° C. The Abs were eluted with 0.2 M glycine pH 2.7, collected in tubes containing 1 M Tris buffer pH 8, subsequently dialyzed against PBS overnight at 4° C. and finally stored at −20° C.

10. IgG and anti-NT4 antibodies depletion

Sera were incubated overnight with glycine saturated CNBr activated sepharose beads (Amersham Bioscience, Uppsala, Sweden). The sera were then incubated overnight with NT4 conjugated sepharose beads or protein A/G agarose. The flow-through was then precipitated as described in the previous section and tested in a cyclic AMP assays.

As shown above, the anti-NT4 IgG has a blocking effect on the MC4-R, resulting in increased appetite (and thus caloric intake), overweight symptoms, and obesity in patients. As such, this auto-antibody against the MC4-R serves as a marker for determining the propensity of a patient to become overweight/obese (as identified, for example, according to the ELISA procedure described herein) and as a research target for the screening of compounds and biologics that will modulate the activity (e.g., neutralize, eliminate, displace the antibodies, etc.) off these auto-antibodies to prevent their blocking effect on the MC4-R (such as through conventional assays and the development of new assays). Such compounds and biologics will then be suitable for use in therapeutic formulations for the prevention and treatment of overeating, overweight conditions, and obesity, and may be provided in conventional formulations (for example, formulations suitable for parenteral, oral, nasal, and other modes of administration) and in combination with other suitable active agents.

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

The contents of all patents, patent applications, published articles, books, reference manuals, texts and abstracts cited herein are hereby incorporated by reference in their entirety to more fully describe the state of the art to which the present invention pertains.

What is claimed is:

1. A biological marker comprising an isolated auto-antibody or fragment thereof that binds to melanocortin-4-receptor or a portion of the melanocortin-4-receptor, wherein said auto-antibody or fragment thereof binds to a portion of the melanocortin-4 receptor comprising SEQ ID NO:2.

2. The biological marker according to claim 1, wherein said portion comprises the NT4 peptide, wherein the NT4 peptide consists of SEQ ID NO:2.

3. The biological marker according to claim 1, wherein said auto-antibody or fragment thereof is detected in a patient's sera by subjecting said sera to an enzyme-linked immunosorbent assay.

4. The biological marker according to claim 3, wherein said enzyme-linked immunosorbent assay is conducted using a peptide comprising the amino acid sequence set forth in SEQ ID NO:2.

5. The biological marker according to claim 1, wherein the isolated auto-antibody or fragment thereof binds to a synthetic NT4 peptide consisting of SEQ ID NO:2.

6. The biological marker according to claim 1, wherein the isolated auto-antibody or fragment thereof recognizes a native melanocortin-4-receptor.

7. The biological marker according to claim 5, wherein the isolated auto-antibody or fragment thereof also recognizes a native melanocortin-4-receptor.

* * * * *

SEQUENCE LISTING

```
<160> NUMBER OF SEQ ID NOS: 2

<210> SEQ ID NO 1
<211> LENGTH: 332
<212> TYPE: PRT
<213> ORGANISM: Rattus norvegicus

<400> SEQUENCE: 1

Met Asn Ser Thr His His His Gly Met Tyr Thr Ser Leu His Leu Trp
1               5                   10                  15

Asn Arg Ser Ser His Gly Leu His Gly Asn Ala Ser Glu Ser Leu Gly
            20                  25                  30

Lys Gly His Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
```

-continued

```
                    85                  90                  95
Asn Gly Ser Glu Thr Ile Val Ile Thr Leu Leu Asn Ser Thr Asp Thr
                100                 105                 110
Asp Ala Gln Ser Phe Thr Val Asn Ile Asp Asn Val Ile Asp Ser Val
                115                 120                 125
Ile Cys Ser Ser Leu Leu Ala Ser Ile Cys Ser Leu Leu Ser Ile Ala
            130                 135                 140
Val Asp Arg Tyr Phe Thr Ile Phe Tyr Ala Leu Gln Tyr His Asn Ile
145                 150                 155                 160
Met Thr Val Arg Arg Val Gly Ile Ile Ile Ser Cys Ile Trp Ala Ala
                165                 170                 175
Cys Thr Val Ser Gly Val Leu Phe Ile Ile Tyr Ser Asp Ser Ser Ala
                180                 185                 190
Val Ile Ile Cys Leu Ile Thr Met Phe Phe Thr Met Leu Val Leu Met
                195                 200                 205
Ala Ser Leu Tyr Val His Met Phe Leu Met Ala Arg Leu His Ile Lys
            210                 215                 220
Arg Ile Ala Val Leu Pro Gly Thr Gly Thr Ile Arg Gln Gly Ala Asn
225                 230                 235                 240
Met Lys Gly Ala Ile Thr Leu Thr Ile Leu Ile Gly Val Phe Val Val
                245                 250                 255
Cys Trp Ala Pro Phe Phe Leu His Leu Leu Phe Tyr Ile Ser Cys Pro
                260                 265                 270
Gln Asn Pro Tyr Cys Val Cys Phe Met Ser His Phe Asn Leu Tyr Leu
            275                 280                 285
Ile Leu Ile Met Cys Asn Ala Val Ile Asp Pro Leu Ile Tyr Ala Leu
            290                 295                 300
Arg Ser Gln Glu Leu Arg Lys Thr Phe Lys Glu Ile Ile Cys Phe Tyr
305                 310                 315                 320
Pro Leu Gly Gly Ile Cys Glu Leu Pro Gly Arg Tyr
                325                 330

<210> SEQ ID NO 2
<211> LENGTH: 15
<212> TYPE: PRT
<213> ORGANISM: Rattus norvegicus

<400> SEQUENCE: 2

Thr Ser Leu His Leu Trp Asn Arg Ser Ser His Gly Leu His Gly
1               5                   10                  15
```